United States Patent

Hayakawa et al.

[11] Patent Number: 5,470,565
[45] Date of Patent: Nov. 28, 1995

[54] COMPOSITION FOR STRENGTHENING ACID RESISTANCY OF TEETH

[75] Inventors: Fumiko Hayakawa, Otsu; Takashi Ando, Kusatsu; Takahide Kimura, Otsu; Yukihiko Hara, Fujieda, all of Japan

[73] Assignee: Mitsui Norin Co., Ltd., Tokyo, Japan

[21] Appl. No.: 216,174

[22] Filed: Mar. 21, 1994

[30] Foreign Application Priority Data

Apr. 19, 1993 [JP] Japan ................... 5-114217

[51] Int. Cl.⁶ ............... A61K 7/16; A61K 7/18; A61K 7/26
[52] U.S. Cl. ................. 424/52; 424/49; 424/58
[58] Field of Search ........................ 424/49–58

[56] References Cited

U.S. PATENT DOCUMENTS

| | | | |
|---|---|---|---|
| 4,108,979 | 8/1978 | Muhler et al. | 424/52 |
| 4,108,981 | 8/1978 | Muhler et al. | 424/52 |
| 4,146,605 | 3/1979 | Ritchey | 424/49 |
| 4,153,732 | 5/1979 | Muhler et al. | 424/49 |
| 4,613,672 | 9/1986 | Hara . | |
| 4,673,530 | 6/1987 | Hara . | |
| 4,840,966 | 6/1989 | Hara et al. . | |
| 4,913,909 | 4/1990 | Hara et al. . | |
| 4,946,950 | 8/1990 | Hara et al. . | |
| 4,976,954 | 12/1990 | Kleber et al. | 424/52 |
| 5,028,412 | 7/1991 | Putt et al. | 424/52 |
| 5,064,640 | 12/1991 | Kleber et al. | 424/52 |
| 5,104,901 | 4/1992 | Shimamura et al. . | |
| 5,135,957 | 8/1992 | Shimamura . | |
| 5,137,922 | 8/1992 | Shimamura et al. . | |
| 5,188,819 | 2/1993 | Kleber et al. | 424/49 |
| 5,204,089 | 4/1993 | Hara et al. . | |

FOREIGN PATENT DOCUMENTS

| | | |
|---|---|---|
| 0067476 | 12/1982 | European Pat. Off. . |
| 0233467 | 8/1987 | European Pat. Off. . |
| 0301975 | 2/1989 | European Pat. Off. . |
| 0415126 | 3/1991 | European Pat. Off. . |
| 0449332 | 10/1991 | European Pat. Off. . |
| 1130566 | 10/1968 | United Kingdom . |

Primary Examiner—Shep K. Rose
Attorney, Agent, or Firm—Frishauf, Holtz, Goodman, Langer & Chick

[57] ABSTRACT

A composition is provided for strengthening the acid resistancy of teeth containing at least one tea polyphenol, a fluoride such as fluorosodium and an aluminum salt, such as aluminum lactate or aluminum nitrate.

16 Claims, 2 Drawing Sheets

COMPOSITION FOR STRENGTHENING ACID RESISTANCY OF TEETH

BACKGROUND OF THE INVENTION

1. Field of the Invention

The present invention relates to a composition which increases an acid resistancy of teeth. More specifically, this invention relates to a composition containing tea polyphenols, which strengthens an acid resistancy of teeth.

This composition can be used in toothpastes, tooth powders or mouthwashes, to effectively increase the acid resistancy of teeth.

2. Description of the Prior Art

It is known that tea contains 300–2000 ppm fluoride of which more than 50% is present in the tea infusion (extract). In comparison to a case of not drinking tea, a case of drinking tea has been found to be preventative in the development of tooth decay and this has been reported to be due to the presence of fluoride in tea.

Fluoride exists as fluoroapatite in the enamel of teeth, and it is well known that it strengthens an acid resistancy of the enamel. However up until now the possibility of an acid resistant composition to strengthen the acid resistancy of teeth has not been put to practical use and thus expectations for the present invention are high.

SUMMARY OF THE INVENTION

The present invention relates to a composition which increases an acid resistancy of teeth, more specifically, a composition containing tea polyphenols which strengthens the acid resistancy of teeth.

DETAILED DESCRIPTION OF THE PREFERRED EMBODIMENTS

Figure 1:
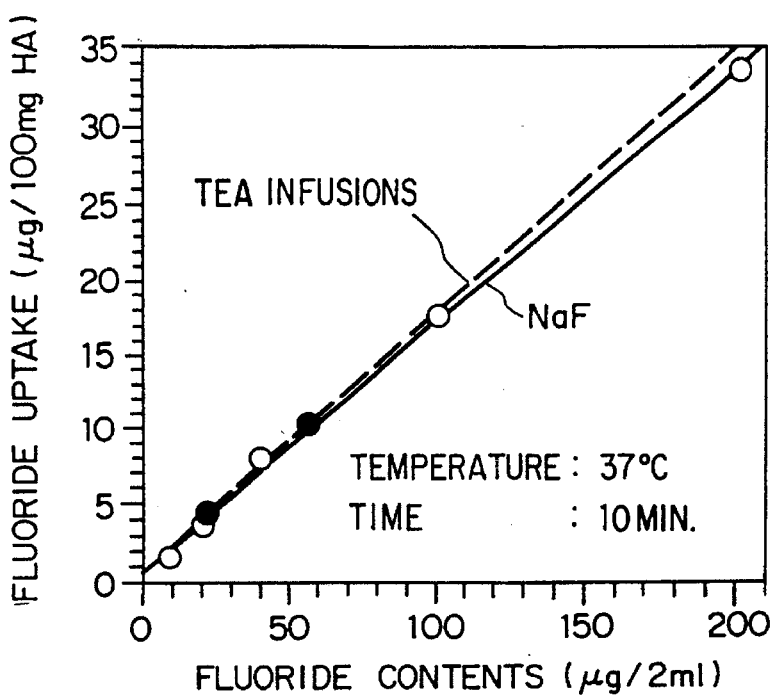
FIG. 1 is a graph which shows a relationship between the fluoride concentration in the solution of Example 1 and the fluoride uptake by hydroxyapatite.

An object of the present invention is to develop a composition which will effectively strengthen the acid resistancy of teeth. The inventors conducted various reseach to investigate the acid resistancy of teeth. As well as investigating the fluoride uptake by hydroxyapatite (hereinunder referred to as HA) and the acid resistancy of fluoride, investigations were conducted into the acid resistancy of substances other than fluoride in the tea infusion, such as organic and inorganic substances. As a result it was found that a composition containing tea polyphenols, fluoride and aluminum salt was effective in strengthening the acid resistancy of teeth and thus the present invention was completed.

That is to say, the present invention relates to a composition containing tea polyphenols, fluoride and aluminum salt, which is characterised by its ability to strengthen the acid resistancy of teeth. The tea polyphenols of the present invention may be in the form of tea catechins or theaflavins, the details and production of which are disclosed in U.S. Pat. Nos. 4,673,530, 4,613,672 and Japanese Patent Kokai 61-130285. The tea polyphenols used may be in a pure form or a mixture thereof. Fluoride used may be in the form of fluorosodium (referred to as NaF from now on) or other fluorides. The aluminum salt may be in an acid or base, nitrate, lactate or acetate form, wherein lactate aluminum is particularly desirable.

Each compound in the composition of the present invention should be in the following concentrations: tea polyphenols 10–2000 ppm, preferably 100–1000 ppm, fluoride 20–1000 ppm, preferably 50–500 ppm, and aluminum 50–2000 ppm, preferably 100–1000 ppm.

The composition of the present invention may be used in toothpastes, tooth powders or mouthwashes. This composition is a natural component of tea, which is consumed daily and there are no problems with its safety. This composition not only has superior acid resistancy but also has a protective effect on the teeth.

EXAMPLES

The present invention will be explained in more detail by way of the following examples,

Example 1

Preparation of Samples

As HA, HA for use in high performance liquid chromatography (HPLC)(product of Wako Chemical Co.) was used. Other chemicals were obtained from Nakalai Tesque Co., NaF solution, product of ORION Co. 940900 standard solution (100 ppm) was diluted. Green tea was extracted in 100 ml of distilled water at a temperature of 90°–93° C. and the filtered liquid was used as the tea extraction liquid. Adjustments were made according to variations in the amount of tea leaves used (2–5 g) and the extraction time (10–20 mins).

100 mg of HA was treated with 2 ml of extracted tea solution or NaF solution and shaken for 10 minutes in a water bath at a constant temperature of 37° C., then separated by centrifugation and the upper layer removed. The residual apatite was rinsed twice in distilled water then dried at a temperature of 37° C. The same procedures were undertaken using distilled water as a control.

Hydrochloric acid was added and dissolved respectively in each of the above HA treated samples and the amount of fluoride uptake by HA was calculated by measuring the amount of fluoride present in the solution. The amount of fluoride uptake in the HA of the NaF solution and in the HA of the tea extraction solution is shown in FIG. 1. As can be seen from the graph, when the fluoride content is the same, the uptake content is also about the same.

Example 2

Figure 2:
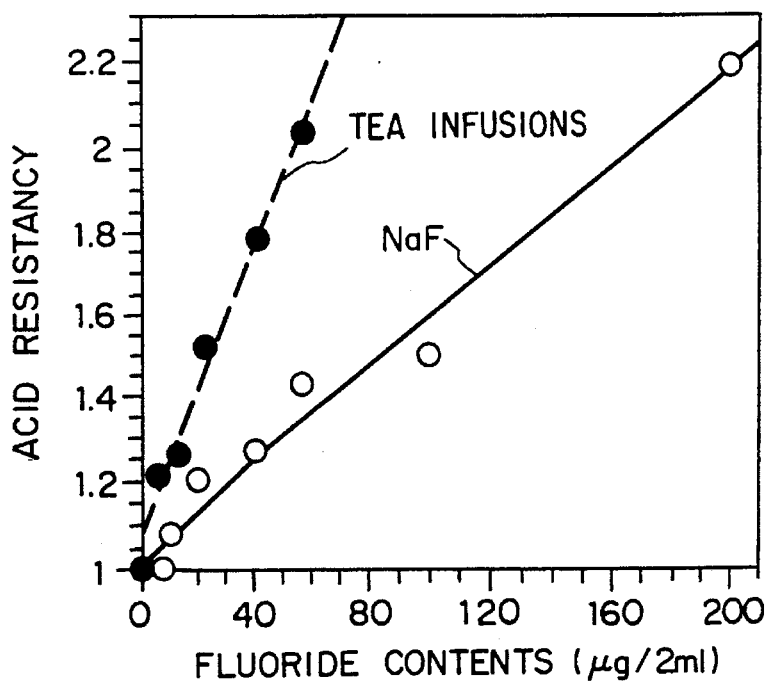
FIG. 2 is a graph which shows a relationship between the fluoride concentration and the acid resistance to hydroxyapatite in Example 2.

10 ml of acetate buffer solution was added to each of the HA treated samples obtained according to the procedures in Example 1, then filtered and the amount of phosphate extracted from the treated solution was measured with a spectrophotometer using the molybdenum method. Results are shown in FIG. 2. As is clear from the graph, acid resistancy strengthens with increased amounts of fluoride. The level of acid resistancy was calculated according to the equation below.

$$\frac{\text{Amount of Phosphorus in Solution of Control Group}}{\text{Amount of Phosphorus in Solution of Test Group}} = \text{Level of Acid Resistancy}$$

Example 3

Figure 3:
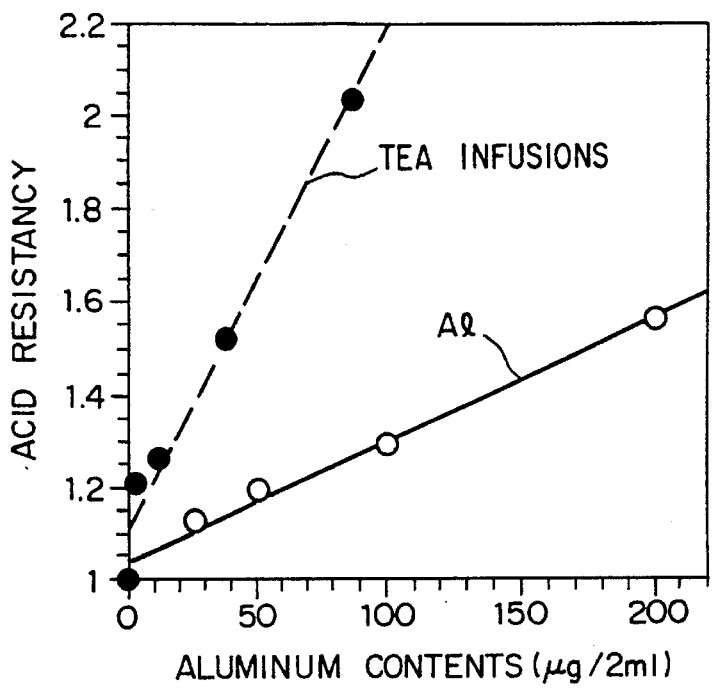
FIG. 3 is a graph which shows a relationship between the aluminum concentration and the acid resistance to hydroxyapatite in Example 3.

Although the amount of fluoride uptake by HA of the solutions of both NaF and green tea infusion was the same, there was a much greater acid resistancy in the green tea infusion. This suggests that something other than fluoride in the green tea infusion is involved in the reaction. Accordingly, the acid resistancy of the organic and inorganic substances in the green tea infusion was investigated. Consequently, it was found that aluminum has acid resistancy. Results are shown in FIG. 3.

Practical Example 1

In further investigations each of the following; NaF (50.0 µg fluoride), Al(NO$_3$)(aluminum 100.0 µg) were added respectively to 2 ml of a phosphate buffer solution containing 5 mg tea polyphenol (in this specification "tea polyphenol" represents Polyphenon 100, the composition of which is shown in Table 2 along with other Polyphenon series) and the same procedures as above were conducted. Results are shown in Table 1.

As is clear from the table, there was no increase in acid resistancy in the polyphenol only solution, but when both fluoride and aluminum salt were added to the solution containing tea polyphenols an increase in acid resistancy was observed.

TABLE 1

Acid Resistancy

| Solution | Phosphorus buffer solution (pH5.6) | Phosphorus buffer solution + Tea polyphenol solution |
|---|---|---|
|  | 1.00 | 1.00 |
| NaF | 1.28 | 1.31 |
| Al(NO$_3$)$_3$ | 1.23 | 1.22 |
| NaF + Al(NO$_3$)$_3$ | 1.55 | 1.85 |

TABLE 2

Composition of catechins in Polyphenons

| Tea catechins | Polyphenon 30 | Polyphenon 60 | Polyphenon 100 |
|---|---|---|---|
| (+)-Gallocatechin(+GC) | — | — | 1.4 |
| (−)-Epigallocatechin(EGC) | 13.0 | 21.0 | 17.6 |
| (−)-Epicatechin(EC) | 3.8 | 7.3 | 5.8 |
| (−)-Epigallocatechin gallate(EGCg) | 15.0 | 29.2 | 53.9 |
| (−)-Epicatechin gallate(EGCg) | 3.5 | 7.9 | 12.5 |
| Total | /35.3 | /65.4 | /91.2 |

Practical Example 2

Figure 4:
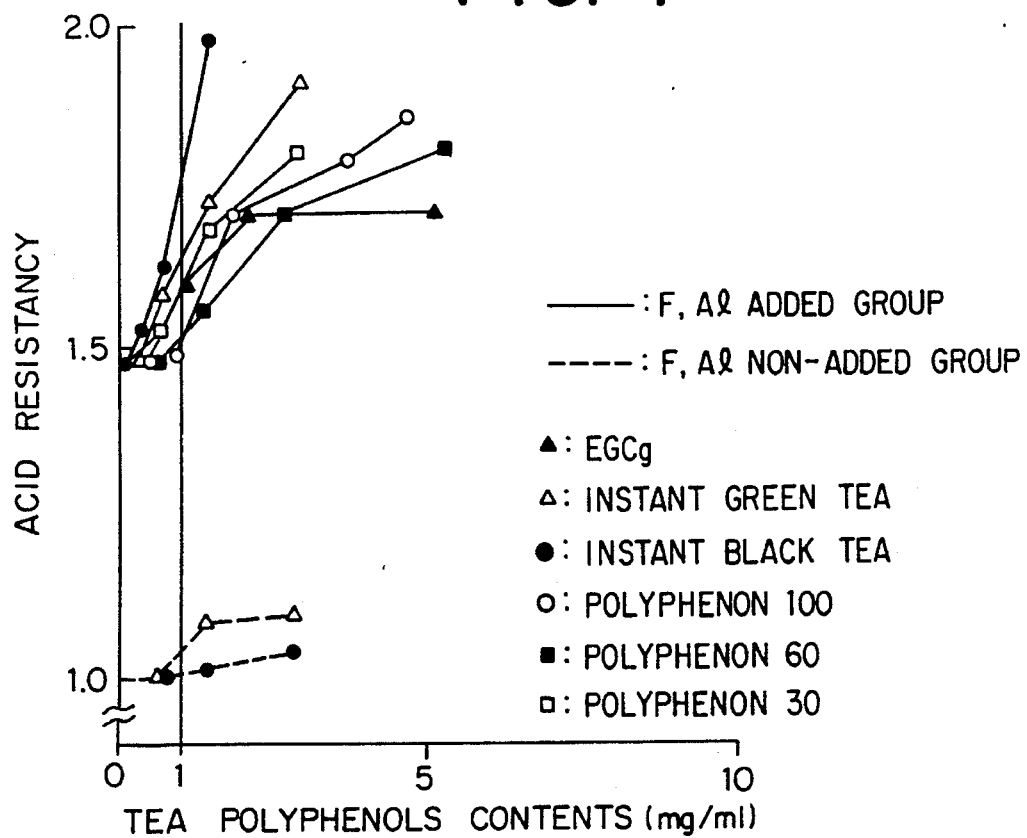
FIG. 4 is a graph which shows a relationship between the polyphenol concentration and the acid resistance in Practical Example 2.

According to the results obtained in Practical Example 1, the same procedures were undertaken with fluoride and aluminum salt added to the other polyphenols listed below. Results are shown in FIG. 4. As is shown in the graph, the addition of fluoride and aluminum salt effectively increased the acid resistancy of all tea polyphenol samples.

Normally the amount of tea polyphenols in a cup of tea is 0.5–1.0 mg/ml. As shown in the graph, an increase in the amount of tea polyphenols will increase the acid resistancy of the teeth.

In the graph EGCg represents the pure form of epigallocatechin gallate and Polyphenon 100 (product of Mitsui Norin) contains more than 90% of tea polyphenols, while Polyphenon 60 (product of Mitsui Norin) contains more than 60% of tea polyphenols and Polyphenon 30 (product of Mitsui Norin) contains more than 30% of tea polyphenols, respectively.

Reference Example 1

A formula for a toothpaste was prepared according to conventional procedures. Units refer to weight. About 1 gram of this toothpaste is used each time when brushing the teeth.

| Secondary calcium phosphate | 45 |
|---|---|
| Sodium carboxymethyl cellulose | 1.0 |
| Glycerin | 20 |
| Lauryl sodium sulfate | 1.0 |
| Aromatic substances (Perfume) | 1.0 |
| Sodium saccharin | 0.2 |
| Tea polyphenol | 0.1 |
| Aluminum nitrate | 0.01–0.1 |
| Sodium fluoride | 0.005–0.05 |
| Made up to 100 with water | |

Reference Example 2

A formula for a mouthwash containing tea polyphenols was prepared according to conventional procedures. Units refer to weight. About 10 ml of the mouthwash are used for each rinse.

| Ethanol | 20 |
|---|---|
| Sodium saccharin | 0.1 |
| Aromatic substances (Perfume) | 1.0 |
| Fatty acid ester of sucrose | 0.5 |
| Tea polyphenols | 0.1 |
| Aluminum lactate | 0.001–0.01 |
| Sodium fluoride | 0.0005–0.005 |

-continued

Made up to 100 with water.

What is claimed is:

1. A composition in the form of a toothpaste, a tooth powder or a mouthwash for strengthening acid resistance of teeth consisting essentially of at least one tea polyphenol, a fluoride and an aluminum salt selected from the group consisting of aluminum nitrate, aluminum sulfate and aluminum lactate.

2. The composition according to claim 1, wherein the at least one tea polyphenol is contained in a concentration of 10–2,000 ppm, the fluoride is contained in a concentration of 20–1,000 ppm and the aluminum salt is contained in a concentration of 50–2,000 ppm.

3. The composition according to claim 1, wherein the at least one tea polyphenol comprises at least one catechin.

4. The composition according to claim 1, wherein the fluoride is fluorosodium.

5. The composition according to claim 1, wherein the at least one tea polyphenol comprises at least one theaflavin.

6. The composition according to claim 1, wherein the fluoride is fluorosodium and the aluminum salt is aluminum lactate or aluminum nitrate.

7. The composition according to claim 1, wherein the at least one polyphenol is contained in a concentration of 100–1,000 ppm, the fluoride is contained in a concentration of 50–500 ppm and the aluminum salt is contained in a concentration of 100–1,000 ppm.

8. The composition according to claim 7, wherein the fluoride is fluorosodium and the aluminum salt is aluminum lactate or aluminum nitrate.

9. The composition according to claim 8, wherein the at least one tea polyphenol comprises epigallocatechin, epicatechin, epigallocatechin gallate and epicatechin gallate.

10. The composition according to claim 9, wherein the at least one tea polyphenol further comprises gallocatechin.

11. A toothpaste comprising the composition according to claim 1, in combination with calcium phosphate, sodium carboxymethyl cellulose, glycerin, lauryl sodium sulfate, aromatic substances, sodium saccharin and water.

12. A mouthwash comprising the composition according to claim 1, in combination with ethanol, sodium saccharin, aromatic substances, a fatty acid ester of sucrose and water.

13. A method for strengthening the acid resistance of teeth by applying to the teeth of a patient in need thereof an effective acid resistance strengthening amount of the composition of claim 1.

14. The method according to claim 13, wherein the at least one polyphenol is contained in a concentration of 100–1,000 ppm, the fluoride is contained in a concentration of 50–500 ppm, the aluminum salt is contained in a concentration of 100–1,000 ppm, the fluoride is fluorosodium, the aluminum salt is aluminum lactate or aluminum nitrate, and the at least one tea polyphenol comprises epigallocatechin, epicatechin, epigallocatechin gallate and epicatechin gallate.

15. The composition according to claim 11, which consists essentially of:

|  | weight % |
|---|---|
| secondary calcium phosphate | 45 |
| sodium carboxymethyl cellulose | 1.0 |
| glycerin | 20 |
| lauryl sodium sulfate | 1.0 |
| aromatic substances | 1.0 |
| sodium saccharin | 0.2 |
| tea polyphenol | 0.1 |
| aluminum nitrate | 0.01–0.1 |
| sodium fluoride | 0.005–0.05, |
| with the balance being water. | |

16. The composition according to claim 12, which consists essentially of

|  | weight % |
|---|---|
| ethanol | 20 |
| sodium saccharin | 0.1 |
| aromatic substances | 1.0 |
| fatty acid ester of sucrose | 0.5 |
| tea polyphenol | 0.1 |
| aluminum lactate | 0.001–0.01 |
| sodium fluoride | 0.0005–0.005, |
| with the balance being water. | |

* * * * *